US008523975B2

(12) United States Patent
Ettlin et al.

(10) Patent No.: US 8,523,975 B2
(45) Date of Patent: Sep. 3, 2013

(54) SALTS OF MINERAL NUTRIENTS STABILIZED WITH AMINO ACIDS AND/OR AMMONIUM SALT, PRODUCTS AND FOOD SUPPLEMENTS THAT CONTAIN THEM AND PROCEDURES FOR OBTAINING SAME

(76) Inventors: Eduardo Walter Ettlin, Buenos Aires (AR); Jose Ruben Boccio, Buenos Aires (AR); Adrian Tomas De Paoli, Buenos Aires (AR); Edgardo Adrian Hager, Buenos Aires (AR); Pablo Adrian De Paoli, Buenos Aires (AR)

( * ) Notice: Subject to any disclaimer, the term of this patent is extended or adjusted under 35 U.S.C. 154(b) by 469 days.

(21) Appl. No.: 12/093,118

(22) PCT Filed: Oct. 13, 2006

(86) PCT No.: PCT/IB2006/003840
§ 371 (c)(1),
(2), (4) Date: May 8, 2008

(87) PCT Pub. No.: WO2007/069072
PCT Pub. Date: Jun. 21, 2007

(65) Prior Publication Data
US 2008/0314107 A1    Dec. 25, 2008

(30) Foreign Application Priority Data
Nov. 11, 2005  (AR) ............................ P20050104763

(51) Int. Cl.
| | |
|---|---|
| *C07C 229/08* | (2006.01) |
| *A23K 1/16* | (2006.01) |
| *A23K 1/175* | (2006.01) |
| *A23L 1/304* | (2006.01) |
| *A23L 1/305* | (2006.01) |
| *C05D 9/02* | (2006.01) |

(52) U.S. Cl.
USPC ............ 71/31; 71/11; 71/33; 71/63; 423/311; 423/463; 423/544; 423/551; 423/554; 423/555; 423/557; 423/558; 424/439; 424/442; 426/74; 426/648; 562/553; 562/575

(58) Field of Classification Search
USPC ............... 71/27, 11, 31, 33, 63; 562/575, 562/553; 426/649, 74, 648; 424/439, 442; 423/311, 463, 544, 551, 554, 555, 557, 558
See application file for complete search history.

(56) References Cited

U.S. PATENT DOCUMENTS

| | | | |
|---|---|---|---|
| 3,928,506 A |  | 12/1975 | Gobert et al. |
| 4,900,561 A | * | 2/1990 | Abdel-Monem et al. ......... 426/2 |
| 5,061,815 A | * | 10/1991 | Leu .............................. 556/118 |
| 5,885,610 A | * | 3/1999 | Anderson ..................... 424/438 |
| 6,071,545 A | * | 6/2000 | Hendler et al. ................. 426/74 |
| 2003/0049284 A1 | * | 3/2003 | Boccio et al. ................. 424/401 |

FOREIGN PATENT DOCUMENTS

| | | |
|---|---|---|
| WO | 01/68087 A | 9/2001 |
| WO | 2004/064536 A | 8/2004 |
| WO | 2004/075654 A | 9/2004 |

OTHER PUBLICATIONS

Hackh's Chemical Dictionary, Fourth Edition (1969), McGraw-Hill Book Company, pp. 10, 11 and 48.*
International Search Report (PCT/IB2006/003840).
* cited by examiner

*Primary Examiner* — Wayne Langel
(74) *Attorney, Agent, or Firm* — Edwards Wildman Palmer LLP

(57) ABSTRACT

Salts of mineral nutrients stabilized with amino acids and/or ammonium salt, product and food supplement in which they are included and procedures of obtention, where the salts are obtained with anions of organic acids or inorganic anions and metallic cations associated with amino acids and/or ammonium salt, in which the invention introduces its general structure:

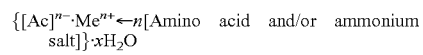

Where ← represents a covalent dative bond,
These new compounds have better taste and more solubility in water, making them more bioavailable.

16 Claims, 2 Drawing Sheets

SALTS OF MINERAL NUTRIENTS STABILIZED WITH AMINO ACIDS AND/OR AMMONIUM SALT, PRODUCTS AND FOOD SUPPLEMENTS THAT CONTAIN THEM AND PROCEDURES FOR OBTAINING SAME

FIELD OF THE INVENTION

The present invention is related to the field of Chemistry and more specifically to chemistry applied to the Food Industry and Dietary Supplements. The invention provides new compounds that are mineral salts stabilized by amino acids and/or ammonium salts, with higher solubility in water, better organoleptic characteristics and greater bioavailability.

DESCRIPTION OF PRIOR ART

The importance of an adequate diet which accomplishes to supplement the requirements of essential minerals for animals as well as for humans is well documented in the literature. There are numerous pieces of work which show the problems caused by the deficiency of essential minerals and how these problems are reversed through the ingestion thereof. The minerals are indispensable for the cellular metabolic processes either as enzyme cofactors, being part of the electron transport chains, etc.

They consist of a group of nutrients (about 30) which do not provide energy to the organism but they have important regulatory functions as well as their structural function as they are part of many tissues. They are constituents of bones and teeth, they control the composition of intracellular and extra liquids and they are part of enzymes and hormones, essential molecules to life. There are two large groups therein: macroelements, so called since they must be furnished in higher quantities by the diet or because they are in higher proportions in the body tissues: calcium, phosphorus, magnesium, sulfur, potassium, sodium and chlorine. Others, such as cobalt, copper, iron, chrome, fluoride, ion, manganese, selenium and zinc, are also necessary, but in lower quantities; thus, they are called microelements or trace elements.

In the same manner, it is important to provide with adequate levels of amino acids. The amino acids are the basis of proteins. The food we consume provides us with proteins. However, such proteins are not normally absorbed in such a composition but they, after their cleavage ("hydrolysis" or breakdown), caused by the digestion process, go through the intestinal wall in the form of amino acids and short-chain peptides, so known as enterohepatic circulation". Those substances are initially incorporated into the bloodstream and, from that place, they are distributed to the tissues which need them to form proteins that are consumed during the vital cycle. It is well-known that out of the 20 known proteic amino acids, 8 are indispensable (or essential) to human life and 2 are "semi-indispensable". These 10 amino acids are required to be incorporated in the organism in its daily food intake and, mainly, when the organism needs them the most: in dysfunctions or disease. The essential amino acids that are the most problematic ones are the tryptophan, lysine and methionine.

It is typically deficient in populations in which cereals and tubers make up the food basis. The deficiency of essential amino acids affect children more than adults. It is worth mentioning that if only one of them (essential amino acids) is lacking, it will not be possible to synthesize any of the proteins in which said amino acid is required. This fact may give rise to different kinds of malnutrition, depending on which the limiting amino acid is.

It is noteworthy that if for a suitable nutrition, a diet must have the adequate levels of essential metals, most of the ways in which said metals are found in nature cannot be used, given the fact that most of the compounds that contain the metals do not have them in a way that can be absorbed, distributed, and used in an efficient way.

The salts of mineral nutrients of mineral or organic acids that are used to fight deficiency syndromes in humans, animals or vegetables have some limiting factors for their use such as the metallic flavor that restricts its acceptance and/or a low solubility in water which restricts its absorption and bioavailability.

The absorption of essential elements depend, in most cases, on the solubility the salts that are used have. Thus, as a general rule, the more solubility, the greater the absorption.

The other relevant factor is the biological behavior of the element once absorbed. This means that the element must fulfill the same metabolic pathways as those known for salts deemed as reference.

The products formed between salts of organic or mineral acids which are produced with amino acids and/or ammonium salts generate a product whose flavor is more pleasant and with an increased solubility.

In the past, different complex compounds of essential metals and amino acids were developed at a 1:1 ratio in order to increase the bioavailability of said metals after their consumption (See U.S. Pat. Nos. 3,941,818, 3,925,433, 3,950,372, 4,021,569 and 4,067,994). In said patents, the resulting compounds form chelates. Chelate is a very simple term which refers to the formation of rings that includes the metallic center in coordination compounds. The formation of this kind of compounds occurs when a ligand with more than one "tooth" is coordinated with the same metallic center.

The salts of this invention are not chelated compounds as the systems mentioned above, but they are stabilized by a dative bond and they have very high solubility, (solutions over 50% b/w or 400 gr per liter of water), which allows to simply add them to the food without changing its aqueous volume.

BRIEF DESCRIPTION OF THE INVENTION

Therefore, an object of this invention is to obtain products of mineral salts of either organic or inorganic acids associated with an amino acid and/or ammonium salts which have a general formula or structure:

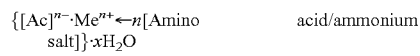

$\{[Ac]^{n-}\cdot Me^{n+}\leftarrow n[\text{Amino acid/ammonium salt}]\}\cdot xH_2O$ where ← represents a dative covalent bond and has a better taste and more solubility in water, which makes it more bioavailable.

Another object of this invention consists in providing with salts of mineral nutrients stabilized with amino acids and/or ammonium salt the metal "$Me^{n+}$" is selected from the group that comprises the following cations: Calcium, Magnesium, Zinc, Iron, Copper, Manganese, Sodium, Potassium, Nickel or Cobalt.

It is also an object of this invention to provide with salts of mineral nutrients stabilized with amino acids and/or ammonium salt where the acid is selected from the group that consists of: Fumaric Acid, Malic Acid, Chloridic Acid or Sulphuric Acid, pure or associated.

Likewise, another object of the present invention are salts of mineral nutrients stabilized with amino acids and/or ammonium salt where the Amino Acid is selected from the group that comprises: Amino Acetic Acid (Glycine) and/or Lysine and the ammonium salt is either organic or inorganic.

Furthermore, another object of this invention is the food supplement that has mineral salts stabilized by amino acids and/or ammonium salt that is able to improve the nutrition and health of human beings and animals, by efficiently increasing the absorption, distribution and use of minerals.

In addition, another object of this invention are mineral nutrient salts stabilized with amino acids and/or ammonium salts where an adequate medium such as waters, carbonated waters, syrups, with natural fruit juices or synthetic juices, liquid or in powder forms, yogurts, dairy desserts, butter, cheese and margarines.

In addition, another object of this invention are mineral nutrient salts stabilized with amino acids and/or ammonium salt where the medium or selected form comprises a pill, effervescent powder, powder, tablets, candy, rigid or soft gelatin capsules for pharmaceutical product presentation, dietary supplement or for veterinary use.

Moreover, another object of this invention are mineral nutrient salts stabilized with amino acids and/or ammonium salt that may be part of the farinaceous products such as bread, pasta, crackers, pastries, dehydrated or concentrate food such as stew, soups, desserts, jelly, laminated cereals, in grains or extruded, cereal bars, whole grain soy or by-products, in flour, in powder form or laminated, and oats.

In addition, another object of the present invention are mineral nutrient salts stabilized with amino acids and/or ammonium salts because when the medium used is aqueous, the resultant solution can be used as foliar fertilizer or other fertilizers.

Likewise, another object of this invention is a procedure for the synthesis of mineral salts stabilized with amino acids and/or ammonium salt, characterized by comprising the following steps:
  a) From the salt previously formed that is solubilized in an aqueous solution of amino acids and/or ammonium salt
  b) The pH is adequately heated and adjusted.
  c) The product formed in the aqueous solution is obtained. By water evaporation, the product can be obtained as dry powder. The solution of the product or the dry powder can be used.

Likewise, another object of this invention is a procedure for the synthesis of copper, iron or manganese salts stabilized with amino acids and/or ammonium salt, characterized by comprising the following stages:
  a) Displacement of calcium salts formed by ferric or ferrous, cupric or manganese ions by incorporating ferric or ferrous, cupric or manganese sulfates respectively.
  b) Precipitation of the calcium sulfate formed, remaining in the solution the ferric or ferrous, cupric or manganese salt of the same anion and bound to the amino acid and/or ammonium salt.
  c) Filter to separate the precipitated calcium sulfate and the product formed remains in the aqueous solution.
  d) Evaporation of water until the product is obtained as dry powder.

Likewise, another object of this invention is a procedure for the synthesis of salts characterized by comprising the following stages:
  a) Solubilization in the aqueous solution of the amino acid and/or ammonium salt in the established relationship of the general formula.
  b) Solution heating and pH adjustment,
  c) The resultant product remains in aqueous solution and can be obtained as dry powder by water evaporation.

where the salts are cupric sulfate, zinc sulfate, potassium sulfate, sodium sulfate, manganese sulfate, ferric and ferrous sulfate, sodium chloride, potassium chloride or calcium chloride.

DETAILED DESCRIPTION OF THE INVENTION

Products of organic anions have been developed such as fumarate, malicate, gluconate, lactate, as well as inorganic anions, such as sulfates or chlorides, in a pure form or combinations of cations such as calcium, magnesium, iron, zinc, copper, manganese, sodium, potassium, cobalt and nickel associated with amino acids such as glycine (amino acetic acid) and/or L-Lysine and/or ammonium salt.

The salts formed show a remarkably higher solubility in water with an acceptable taste, when it is assessed against the non-associated salt taken as a standard and with the same metal ion concentration that is necessary to provide with.

Theses characteristics in the products formed make it very useful for the provision of mineral macro and micronutrients in diet supplements, medicine products and in food and drinks conveniently fortified or enriched.

The general chemical structure of the compounds formed corresponds to the following diagram:

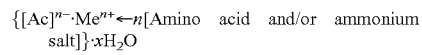

$\{[Ac]^{n-} \cdot Me^{n+} \leftarrow n[\text{Amino acid and/or ammonium salt}]\} \cdot xH_2O$ where:
n takes values from 1 to 3, and
x takes values from 0 to 10.

The metal $Me^{n+}$ can be Calcium, Magnesium, Zinc, Iron, Copper, Manganese, Sodium, Potassium, Cobalt or Nickel.

The acid can be Fumaric Acid, Lactic Acid, Gluconic Acid, Malic Acid, Chloridic Acid or Sulfuric Acid, pure or associated.

The Amino Acid can be Amino Acetic Acid (Glycine) and/or Lysine.

The ammonium salt can be organic or inorganic.

Figure 1:
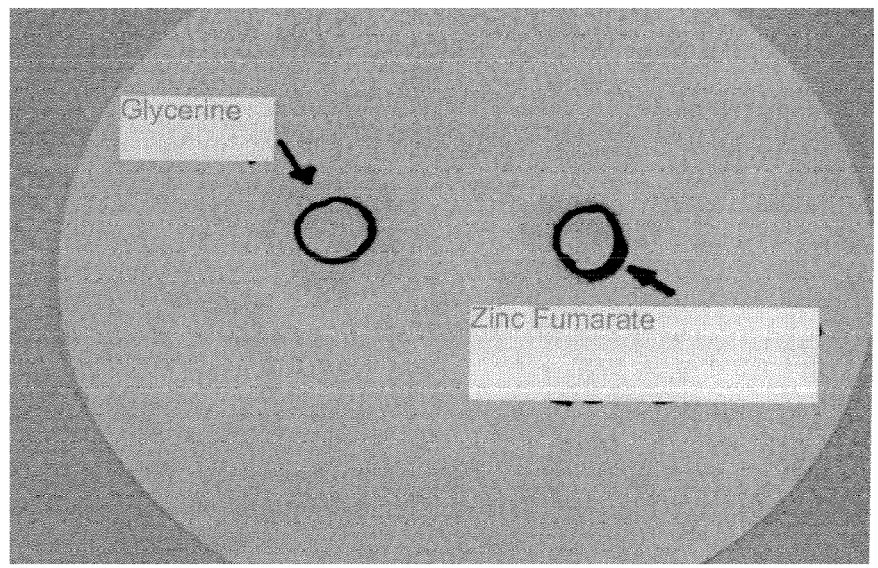
FIG. 1 shows the sample of zinc fumarate associated with glycine (Biofumarate of Zn) and the glycine standard.
Figure 2:
FIG. 2 shows the sample of zinc fumarate associated with glycine (Biofumarate of Zn) and the glycine standard after the reaction with ninhydrin.

Having the structure of the product formed been studied, it shows the formation of a product in which the aminic nitrogen of the amino acid and/or ammonium salt is bound to the metal by a coordinated dative bond (See FIGS. 1 and 2)

The functional identification of the coordinated dative bond with the aminic nitrogen of the amino acid was characterized by the reaction with ninhydrin (See FIGS. 1 and 2).

FIG. 1 shows the sample of zinc fumarate associated with the glycine (Biofumarate of Zn) and the glycine standard.

FIG. 2 shows the same sample after the reaction with ninhydrin. The violet color of the glycine standard shows that the glycine is free. The yellow colour corresponds to the reaction of the product restored with the ninhydrin, said reaction shows that the carboxylic group of the glycine is free while the aminic group is associated with the metal (Zn in this case). Should the glycine be free, the colour would have been violet. However, if both functional groups of the glycine (amino and carboxylic) had been bound to the metal (as it happens in the case of the amino chelate compounds) there would not have been any reaction with ninhydrin and it would be colorless.

The product is characterized for not forming a chelate and the salt obtained has better characteristics of solubility and taste than the salt alone.

Therefore, the object of this invention is to obtain products of mineral salts of organic or inorganic acids associated with an amino acid and/or ammonium salts which have a general structure:

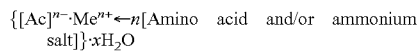
$\{[Ac]^{n-} \cdot Me^{n+} \leftarrow n[\text{Amino acid and/or ammonium salt}]\} \cdot xH_2O$ which have better taste and more solubility in water, making them more bioavailable.

It can comprise the formation thereof:
- a) From the salt previously formed that is solubilized in an aqueous solution of amino acids and/or ammonium salt, the pH is heated and adjusted in an adequate way. The product formed in aqueous solution is obtained. By water evaporation the product can be obtained as dry powder The solution of the product or the dry powder can be used.
- b) Calcium salts formed can be displaced by ferric or ferrous, cupric or manganese ions by adding ferric or ferrous, cupric or manganese sulfate respectively. The calcium sulfate formed precipitates, the ferric or ferrous, cupric or manganese salt of the same anion remains in the solution and bound to the amino acid and/or ammonium salt. It is filtered to separate the precipitated calcium sulfate and the product formed remains in aqueous solution that can be turned into dry powder by water evaporation.
- c) The salts such as cupric sulfate, zinc sulfate, potassium sulfate, sodium sulfate, manganese sulfate, ferric sulfate or ferrous sulfate can also be formed by solubilizing them in the aqueous solution of amino acids in the established relationship of the general formula, by heating the solution and adjusting the pH. The resultant product remains in aqueous solution and can be obtained as dry powder by water evaporation.
- d) The salts such as cupric chloride, zinc chloride, potassium chloride, sodium chloride, manganese chloride, ferric chloride or ferrous chloride can also be formed by solubilizing them in the aqueous solution of amino acids in the established relationship of the general formula, by heating the solution and adjusting the pH. The formed product remains in aqueous solution and can be obtained as dry powder by water evaporation.

Comparative Data of Solubility:
1. Ferrous fumarate (Ref. 4094 Index Merck XII Ed., Page 686) SP 169.90, content of $Fe^{++}$ 32.87%, AW Fe 55,847. Solubility in water at 25° C.: 1.4 grams per liter of water. It allows 0.460 gr $Fe^{++}$ (ferrous) per liter of water Ferrous Fumarate stabilized with 2 moles of Glycine (Amino acetic acid):
It contains
Ferrous Fumarate 169.90 gr (53.09%).
Glycine (2×75.07) 150.14 gr (46.91%).
Product 320.04 gr (17.45% of Fe).
Solubility in water at 25° C., as Ferrous Fumarate stabilized with 2 moles of Glycine: 54.6 grams per liter.
As Ferrous Fumarate (53.9%): 29.0 grams/liter. It allows: 9.53 grams $Fe^{++}$ (Ferrous) per liter of water Solubility increase per liter: 20.7 times (results from: 9.53 gr of Fe/0.460 gr of Fe).
The data stated clearly shows the solubility increase in water of a salt such as the Ferrous Fumarate that is used as a source of mineral micronutrient iron, in dietary supplementation in fortified food.

2. Calcium Fumarate $3H_2O$ Ref. manufacturer Bartek Inc., Canada) SP 208.18 calcium content 19.25% (aw Ca 40.08) Solubility in water at 25° C.: 1.22 grams per liter: it allows to solubilize 0.234 gram $Ca^{++}$/liter of water Calcium Fumarate $3H_2O$ stabilized with 2 moles of glycine (amino acetic acid) Calcium Fumarate $3H_2O$: 208.18 58.09%2 Glycine: 2×75.07 150.14 41.91% 358.32 11.18% as Calcium. Solubility in water as Calcium Fumarate stabilized with 2 moles of Glycine: 50.0 grams/liter As Calcium Fumarate: 29.045 grams/liter As Calcium (19.25%): 5,591 gr Calcium/liter Solubility increase: 23.9 times (results from: 5.591/0.234 gr) as Calcium

EXAMPLES OF REALIZATION

The following specific examples provided herein are used to illustrate the nature of this invention. These examples are intended for illustrative purposes only and should not be interpreted as limiting factors for the invention claimed herein.

Example No 1

Preparation of the Calcium Salt as Calcium Fumarate with Amino Acetic Acid (Glycine) Solution at 5.0%

1. A 2000 CC beaker must be filled with:
Purified water: 1800 gr. Weigh calcium hydroxide (minimum 95%): 24.84 gr (check purity and humidity) Scatter homogenously.
2. Weigh Amino Acetic Acid (minimum 98.5%): 47.92 grams and add it. Heat with stirring in a bain-marie.
3. Weigh fumaric acid (minimum 99.0%): 37.05 grams and add it. Continue heating it with stirring in bain-marie, in order to keep the solution between 60 and 85° C., over no longer than 30 minutes.
4. Take a sample and adjust the pH of the solution to 5% p/w to 6.5 (6.2 to 6.8) using calcium hydroxide or fumeric acid when deemed necessary.
5. Once the pH has been adjusted, the calcium is assessed and the result must be not less than 0.56 gr % Calcium.
6. The solution obtained is filtered through paper and preferably with a product to help the filtration, thus obtaining a crystalline solution.
7. The solution obtained can be dried with hot air until it gets dry. The powder may contain no more than 15% as crystallization water.
8. About 100 to 112 grams of the product is obtained, depending on the water of crystallization.
9. At an industrial scale, the solution is prepared in adequate reactors and it is dried through a spray system.

Example 2

Preparation of a Ferrous Salt, as Ferrous Fumarate with Amino Acetic Acid (Glycine), Solution 10%

1. A 2000 CC beaker must be filled with: Purified water: 900 mL or gr. Weigh calcium hydroxide (minimum 95%): 24.84 gr (check purity and humidity) Scatter homogenously with stirring.
2. Weigh Amino Acetic Acid (minimum 98.5%): 47.92 grams and add it. Heat with stirring in a bain-marie.
3. Weigh the fumaric acid (minimum 99.0%) 37.05 grams and add it. Continue heating it with stirring in bain-marie, in order to keep the solution between 60 and 85° C., over no longer than 30 minutes.

4. Take a sample and adjust the pH of the solution to 5% p/w to 4.5.
5. Once it has been adjusted, the pH is added: Ferrous Sulfate 7H$_2$O (minimum 19.8% Fe$^{++}$): 88.74 gr The heating is cut, continuing the stirring not less than 30 minutes.
6. It is left to settle, the supernatant is filtered through the filtration process, a crystalline dark green solution is obtained.
   The solution contains about 1.75% as iron and 10% (9.5 to 10.5%) as product in solution.
7. The solution obtained can be dried by hot air until it gets dry. The loss for drying at 105-108° C. must be not higher than 10%.
8. About 100 to 115 grams of the product is obtained, depending on the water of crystallization.
9. At an industrial scale, the solution is prepared in adequate reactors and it is dried through a spray system.

The invention claimed is:

1. A mineral salt associated with an amino acid and/or ammonium salt, comprising:
   a salt comprising an anion and a metallic cation, wherein said anion is derived from an organic or inorganic acid; and
   an amino acid and/or ammonium salt, wherein the amino acid and/or ammonium salt is associated with said metallic cation,
   wherein the metallic cation is bound to the anion by an ionic bond and is further bound to the amino group of the amino acid or ammonium salt by a covalent dative bond, thereby forming a stabilized mineral salt having the general formula:

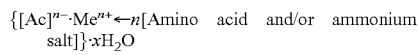

where:
Ac is an anion derived from an organic or inorganic acid;
Me is a metal;
n is a value from 1 to 3; and
x is a value of 0 to 10.

2. The mineral salt according to claim 1, wherein the metallic cation is a cation of a metal selected from the group consisting of calcium, magnesium, zinc, iron, copper, manganese, sodium, potassium, nickel, and cobalt.

3. The mineral salt according to claim 1, wherein the acid is fumaric acid, malic acid, gluconic acid, lactic acid, citric acid, acetic acid, propionic acid, hydrochloridic acid, sulfuric acid, phosphoric acid or any combination thereof.

4. The mineral salt according to claim 1, wherein the amino acid is amino acetic acid or lysine, and the ammonium salt is organic or inorganic.

5. The mineral salt according to claim 1, wherein the salt is covered or encapsulated.

6. The mineral salt according to claim 1, wherein the salt is useful for the treatment of deficiency diseases in human beings, animals and vegetables, and provides a source of macro or micro mineral in an acceptable vehicle for consumption.

7. A food supplement comprising:
   a mineral salt of claim 1, wherein the food supplement is capable of increasing absorption, distribution and use of minerals in an animal, thereby improving nutrition or health of the animal.

8. The food supplement according to claim 7, wherein the food supplement is contained in a medium selected from the group consisting of water, carbonated water, syrup, natural fruit juice, synthetic juice, yogurt, dairy dessert, butter, and cheese margarine, and the food supplement is in liquid or powder form.

9. The food supplement according to claim 7, wherein the food supplement is contained in a medium selected from the group consisting of pills, tablets, effervescent powder, powder, tablets, candy, rigid gelatin capsules, and soft gelatin capsules.

10. The food supplement according to claim 7, wherein the food supplement is included in at least one product selected from the group consisting of a farinaceous product, bread, pasta, crackers, pastries, dehydrated and concentrate food, wherein said concentrate food is selected from the group consisting of stew, soups, desserts, jelly, laminated cereals, grains, extruded, cereal bars, whole grain soy or by-products thereof, flour, and powder or laminate oats.

11. A fertilizer product comprising the mineral salt of claim 1.

12. A procedure for the synthesis of a mineral salt according to claim 1, the procedure comprising the steps of:
   a) solubilizing the salt comprising the anion and metallic cation in an aqueous solution comprising an ammonium salt and/or amino acids;
   b) heating the aqueous solution obtained from step a);
   c) adjusting the pH of the aqueous solution; and
   d) obtaining a mineral salt product formed from step c).

13. The procedure according to claim 12, further including the step of evaporating the water in the aqueous solution until forming the product in a dry powder form.

14. A procedure for the synthesis of a mineral salt according to claim 1, wherein said metallic cation is a cation of copper, iron or manganese, the procedure comprising the steps of:
   a) displacing calcium salts formed by ferric or ferrous, cupric or manganese ions by adding ferric or ferrous, cupric or manganese sulfate respectively,
   b) Precipitating calcium sulfate formed of step a), thereby remaining the ferric or ferrous, cupric or manganese salt of the same anion in the solution and bound to the amino acid and/or ammonium salt;
   c) filtering the solution to separate precipitated calcium sulfate from the aqueous solution;
   d) evaporating the water of the aqueous solution until a dry powder is formed.

15. The procedure according to claim 14, wherein the salts are selected from the group consisting of: cupric sulfate, zinc sulfate, potassium sulfate, sodium sulfate, manganese sulfate, and ferrous or ferric sulfate.

16. The procedure according to claim 14, wherein the salts are selected from the group consisting of sodium chloride, potassium chloride, and calcium chloride.

* * * * *